Figure 1:
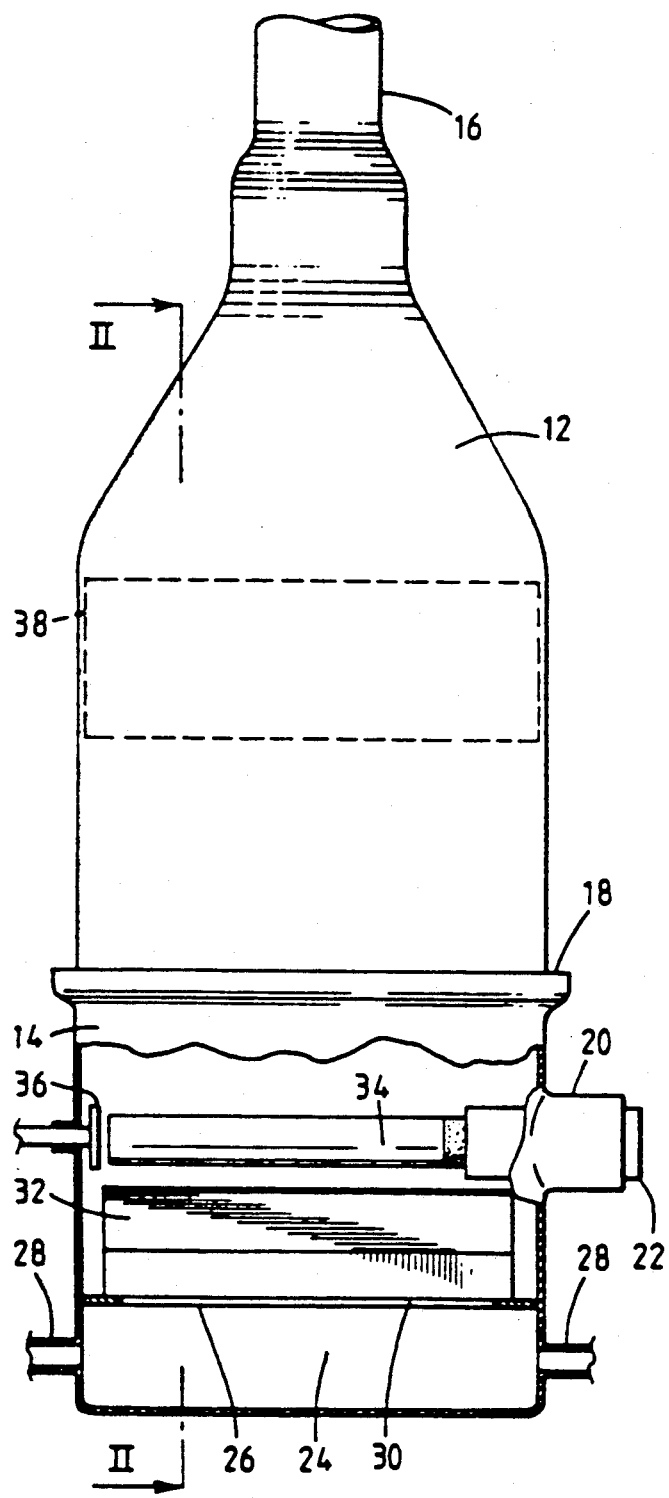

United States Patent [19]

Piadé et al.

[11] Patent Number: 5,113,689

[45] Date of Patent: May 19, 1992

[54] CIGARETTE SIDESTREAM SMOKE COLLECTION APPARATUS

[75] Inventors: Jean-Jacques Piadé, Neuchâtel; Gregor Nicholas, Saint-Blaise, both of Switzerland

[73] Assignee: Fabriques de Tabac Reunies, S.A., Neuchatel, Switzerland

[21] Appl. No.: 578,187

[22] Filed: Sep. 6, 1990

[30] Foreign Application Priority Data

Sep. 11, 1989 [GB] United Kingdom ............... 8920496

[51] Int. Cl.$^5$ .................................... G01M 3/36
[52] U.S. Cl. ................... 73/23.31; 73/23.21; 73/38
[58] Field of Search ............ 73/23.31, 38, 23.21

[56] References Cited

U.S. PATENT DOCUMENTS

| 3,200,648 | 8/1965 | Waggaman | 73/23.31 |
|---|---|---|---|
| 3,460,374 | 5/1969 | Parks | 73/23.31 |
| 4,213,327 | 6/1980 | Prescott et al. | 73/38 |
| 4,400,972 | 8/1983 | Wiethaup | 73/38 |
| 4,589,775 | 5/1986 | Milhous, Jr. et al. | 356/439 |
| 4,596,134 | 6/1986 | Weatherly | 73/38 |

FOREIGN PATENT DOCUMENTS 48809  9/1988  Japan .................. 73/23.21

Primary Examiner—Hezron E. Williams
Assistant Examiner—Craig Miller
Attorney, Agent, or Firm—Jeffrey H. Ingerman

[57] ABSTRACT

Sidestream smoke collection apparatus comprises a smoking chamber 14 including a plenum chamber 24, air inlets 28, an internal wall 26 having slits 30 for the passage of air, a cigarette holder 22 above the internal wall 26, an outlet pipe 16 above the cigarette holder, an upper deflector 38 between the cigarette holder and the outlet and a lower deflector 32 between the cigarette holder and the internal wall. This dispatch of air inlet and outlet and deflectors allows more efficient collection of sidestream smoke.

9 Claims, 1 Drawing Sheet

U.S. Patent

May 19, 1992

5,113,689

CIGARETTE SIDESTREAM SMOKE COLLECTION APPARATUS

Sidestream smoke analysis is a two-step process: it involves the collection of the sidestream smoke emitted by a cigarette and its subsequent trapping for analysis.

Many collection apparatuses have been used by researchers in this field, mostly for single cigarette analysis.

Known collection apparatus, however, disturbs the way in which the cigarette smokes, leading to inaccurate measurement of sidestream smoke composition. Further, few of the devices are suitable for handling large sample numbers. Thus they can be used in research studies but cannot perform analysis of a number of cigarettes, for example to investigate the variability of product.

It is, therefore, desirable to provide a sidestream smoke collection apparatus which is efficient in collecting the sidestream smoke, does not disturb the smoking of the cigarette and can be used to achieve a high sample throughput.

In order to meet the efficiency and non-disturbance criteria, the apparatus should preferably:
  not allow any sidestream smoke to escape;
  impart minimal alteration to the smoke as it is conveyed to the analytical or trapping system; and
  not alter the way the cigarette is smoked.

Suitability for high sample throughput implies that the system should:
  allow for several collectors to be operated side-by-side on a multi-port smoker;
  sample the smoke in a minimal volume of air; and be simple to operate.

The present invention provides apparatus for collecting sidestream smoke from a cigarette comprising a housing for the cigarette, which is supported for smoking above a first, lower, deflector to prevent incoming ambient air, from below, impinging directly on the cigarette, the housing having an exhaust above the cigarette for withdrawal of sidestream smoke and a second, upper, deflector disposed between the cigarette and the exhaust port, to channel the smoke substantially to a middle zone of the port.

Preferably the housing has a longitudinal exhaust port above the cigarette.

Figure 2:
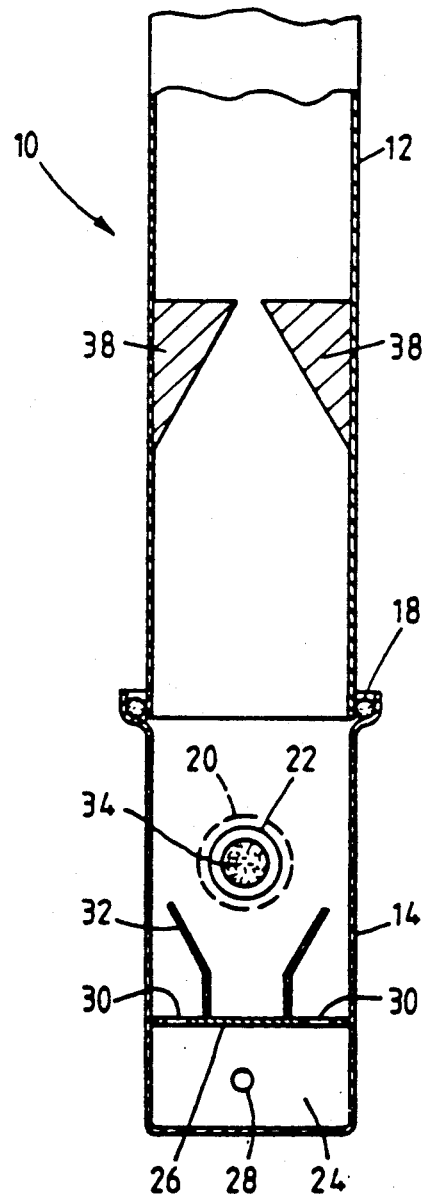

The invention will be further described, by way of example, with reference to the drawings, in which:

FIG. 1 shows a side elevation of a preferred sidestream smoke collector according to the invention containing a cigarette with the front wall of the lower chamber removed to show the interior of the collector; and FIG. 2 shows a cross-section on line II—II of FIG. 1.

The collector 10 comprises an upper hood 12 a lower smoking chamber 14, and a smoke outlet pipe 16. The hood 12 is of glass, so that the progress of the smoking of the cigarette and the behavior of the smoke may be observed, while the smoking chamber 14 is of steel. An O-ring seal 18 seals the hood to the smoking chamber.

The smoking chamber 14 has an opening 20 in one end wall for reception of a cigarette holder 22 of conventional design. This is connected to a conventional smoking machine, not shown.

The lower region 24 of the smoking chamber 14, below the opening 20 for the cigarette holder, is divided from the upper region by an internal wall 26. This lower region 24 is a plenum chamber, supplied with ambient air through tubes 28 in the end wall of the smoking chamber, and communicating with the upper region of the smoking chamber through longitudinal slits 30 about 4 mm wide down either side of the internal wall 26. Instead of the tubes 28, the bottom wall of the smoking chamber 14 may be absent, allowing air to enter the plenum chamber 24.

The internal wall 26 supports a lower deflector 32, which is about 1.6 cm high, beneath a cigarette 34 in the holder 22 in the opening 20. The deflector comprises two plates either side of and below where the cigarette 34 is held, at angle to each other, to form a generally V section deflector below the cigarette extending substantially the length of the smoking chamber 14. The lower portions of each plate of the defector 32 extend substantially vertically to support the deflector on the wall 26 between the plenum chamber 24 and the upper region of the smoking chamber 14. The deflector is at least as wide as the cigarette, preferably about 2 cm at the top, so it extends almost across the width (about 3 cm) of the smoking chamber 14, leaving a narrow passage, between 2 and 5 mm wide, along each side for air to reach a cigarette 34. The radial distance of the deflector plates from a cigarette is between 5 mm and 20 mm, preferably about 8 mm.

A cigarette lighter 36 is provided in the smoking chamber which can be moved into and out of contact with the cigarette 34 in the holder 22.

The hood 12 fits over the open top of the smoking chamber 14 and is sealed thereto by the O-ring 18. The end walls of the hood 12 taper to the outlet pipe 16.

The lower region of the hood 12, below the taper, contains an upper deflector 38, between 2 cm and 10 cm, and preferably about 6 cm, above the cigarette 34, in the form of two triangle section plastic strips each extending longitudinally down one side of the hood 12 substantially the whole length of the hood so that the lower region tapers to a slit between 2 mm and 10 mm wide, preferably about 4 mm wide through which smoke can enter the outlet pipe 16. The precise shape of the upper deflector is not critical, but preferably the sloping faces of the triangle section strip subtend an angle of at least 20° with the horizontal.

In use, a holder 22 containing a cigarette 34 is placed in the opening 20 in the end wall of the smoking chamber 14. The holder is connected through a conventional filter (not shown) to a conventional smoking machine and smoke analysis apparatus. The upper end of the outlet pipe 16 of the hood 12 is connected to a pump, a conventional filter and a conventional smoke analysis apparatus (not shown).

The cigarette 34 is smoked by the apparatus, the sidestream smoke is drawn at the rate of about 4 l/minute into the lower region of the hood and deflected by the upper deflectors 38 into the central region of the tapered portion of the hood and into the output pipe 16.

If desired, an automatic cigarette extinguisher may be incorporated into the collector. The extinguisher may, for example, comprise an infra red radiation sensor, which detects the cigarette ember when it has reached a predetermined position, and activates a nitrogen source to introduce nitrogen gas into the plenum chamber 22.

The plenum chamber 24 in the smoke chamber 14, with the longitudinal slits 30 in the internal wall 26 and the lower deflector 32, together with the upper deflector 38 in the hood and the tapered shape of the hood, ensure that the flow of sidestream smoke into the exhaust pipe is essentially undisturbed and closely mimics that observed in normal smoking. The slit formed by the deflectors 38 in the hood 12 acts as a one-way valve, preventing smoke from returning from the exhaust pipe 16 to the smoking chamber 14. No sidestream smoke escapes from the collector 10 other than through the outlet pipe 16.

The collector of the invention collects substantially all the sidestream some does not alter the way the cigarette is smoked and imparts minimal alteration to the sidestream smoke as it moves to the analytical apparatus.

The shape and manner of operation of the collectors 10 of the invention enable several to be mounted on a single gantry (not shown), which can move back and forth, for example on a track, to move the collectors 10 onto any away from the cigarette holders of a smoking machine. Each collector 10 is connected through a filter to an analytical apparatus. This arrangement allows the simultaneous sampling of sidestream smoke from many cigarettes. Since each collector 10 is almost closed, apart from the ambient air tubes 28 opening into the plenum chamber 24 of the smoking chamber 14, the air intake can be readily controlled, and there is no loss of sidestream smoke from the collector. The provision for lighting and extinguishing cigarettes in the collector without disturbance allows more effective sidestream smoke sampling.

We claim:

1. Apparatus (10) of collecting sidestream smoke from a smoking article (34) such as a cigarette, comprising:
   a housing (12, 14) having a holder (22) extending into the housing from outside for holding a smoking article allowing the smoking article to be smoked from outside the housing and an air inlet (24, 28) to the lower portion of the housing below the holder;
   a lower air deflector (32) within the housing below the holder (22) to deflect air from the inlet (24, 28) around a smoking article in the housing;
   an outlet (16) from the upper portion of the housing above the holder (22) for the withdrawal of air and smoke therefrom, and an upper air deflector (38) within the housing above the holder (22) being so disposed as to deflect air and smoke into the exhaust.

2. Apparatus (10) according to claim 1 in which the housing comprises a smoking chamber (14) including the holder (22) and the air inlet (24) surmounted by and removably sealed to a hood (12) including the outlet (16).

3. Apparatus (10) according to claim 1 or 2 in which the air inlet comprises a plenum chamber (24) in the lower portion of the housing (12, 14) below the holder (22).

4. Apparatus (10) according to claim 1 in which the lower air deflector (32) comprises two plates either side of and below where the smoking article (34) is held, the plates being joined together to prevent air from impinging directly from below a smoking article held in the apparatus.

5. Apparatus (10) according to claim 1 in which the upper air deflector (38) forms an upwardly tapering passage extending longitudinally above a smoking article (34) held in the holder (22) for air and smoke passing through the upper portion (12) of the housing to the exhaust (16).

6. Apparatus (10) according to claim 1 including a lighter (36) to light a smoking article (34) held in the hosing (12, 14).

7. Apparatus (10) according to claim 1 including extinguishing means to extinguish a smoking article (34) in the housing (12, 14).

8. Apparatus (10) according to claim 1 in which the holder (22) for a smoking article (34) is detachable from the housing (12, 14).

9. Apparatus for collecting sidestream smoke from a plurality of smoking articles comprising a plurality of apparatus according to claim 8, the housings (12, 14) of which are mounted on a gantry which is movable relative to a smoking machine to move the holders (22) into and out of the housings for loading and removal of smoking articles (34).

* * * * *